US00PP14624P39

(12) United States Plant Patent
Noodelijk

(10) Patent No.: US PP14,624 P3
(45) Date of Patent: Mar. 23, 2004

(54) CHRYSANTHEMUM PLANT NAMED 'POWELL'

(50) Latin Name: *Chrysanthemum morifolium*
Varietal Denomination: Powell

(75) Inventor: Robert Noodelijk, Woubrugge (NL)

(73) Assignee: Chrysanthemum Breeders Association, N.V. (NL)

( * ) Notice: Subject to any disclaimer, the term of this patent is extended or adjusted under 35 U.S.C. 154(b) by 42 days.

(21) Appl. No.: 10/175,868

(22) Filed: Jun. 21, 2002

(65) Prior Publication Data

US 2003/0009808 P1 Jan. 9, 2003

(30) Foreign Application Priority Data

Jun. 28, 2001 (NL) ..... CHR 3270

(51) Int. Cl.[7] ..... A01H 5/00

(52) U.S. Cl. ..... Plt./295

(58) Field of Search ..... Plt./295

*Primary Examiner*—Bruce R. Campell
*Assistant Examiner*—Anne Marie Grunberg

(74) *Attorney, Agent, or Firm*—Parkhurst & Wendel, L.L.P.

(57) ABSTRACT

A Chrysanthemum plant named 'Powell' characterized by its large sized blooms with huge yellow ray-florets and green disc florets.

3 Drawing Sheets

Genus and species: *Chrysanthmum morifolium.*

BACKGROUND OF THE INVENTION

'Powell' is a product of a breeding-program which had the objective of creating new chrysanthemum cultivars with a daisy type flower, a 5 week response and a medium plant height. The new plant of the present invention comprises a new and distinct cultivar of Chrysanthemum plant. 'Powell' is a seedling from a cross in a breeding program maintained under the control of inventor. The female parent is 'Miramar' (U.S. Plant Pat. No. 7,469), the male parent is 94.1106, an unpatented, unamed seedling. The male parent is not available to inventor for description. A comparison with the female parent is made in this description. The new and distinct cultivar was discovered and selected as a flowering plant within the progeny of the stated cross by Rob Noodelijk in a controlled environment (greenhouse) in Rijsenhout Holland in April 1997. The first act of asexual reproduction of 'Powell' was accomplished when vegetative cuttings were taken from the initial selection in June 1997 in a controlled environment in Rijsenhout Holland.

SUMMARY OF THE INVENTION

The present invention is a new and distinct variety of chrysanthemum bearing large sized blooms with huge yellow ray-florets and green disc florets.

BRIEF DESCRIPTION OF THE DRAWINGS

The present invention of a new and distinct variety of chrysanthemum is shown in the accompanying drawings, the color being as nearly true as possible with color photographs of this type.

DESCRIPTION OF THE INVENTION

Figure 1:
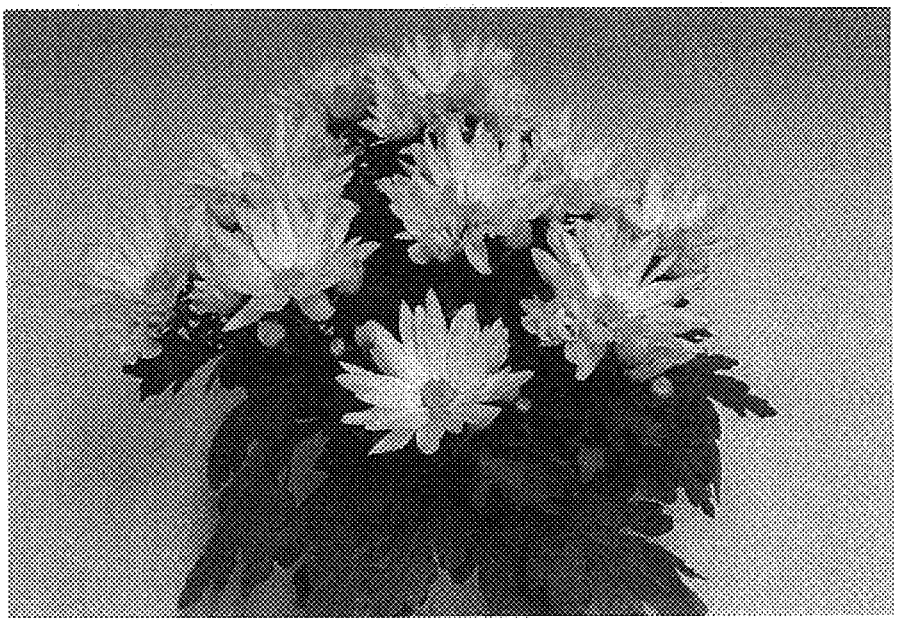
FIG. 1 shows a plant of the cultivar in full bloom.
Figure 2:
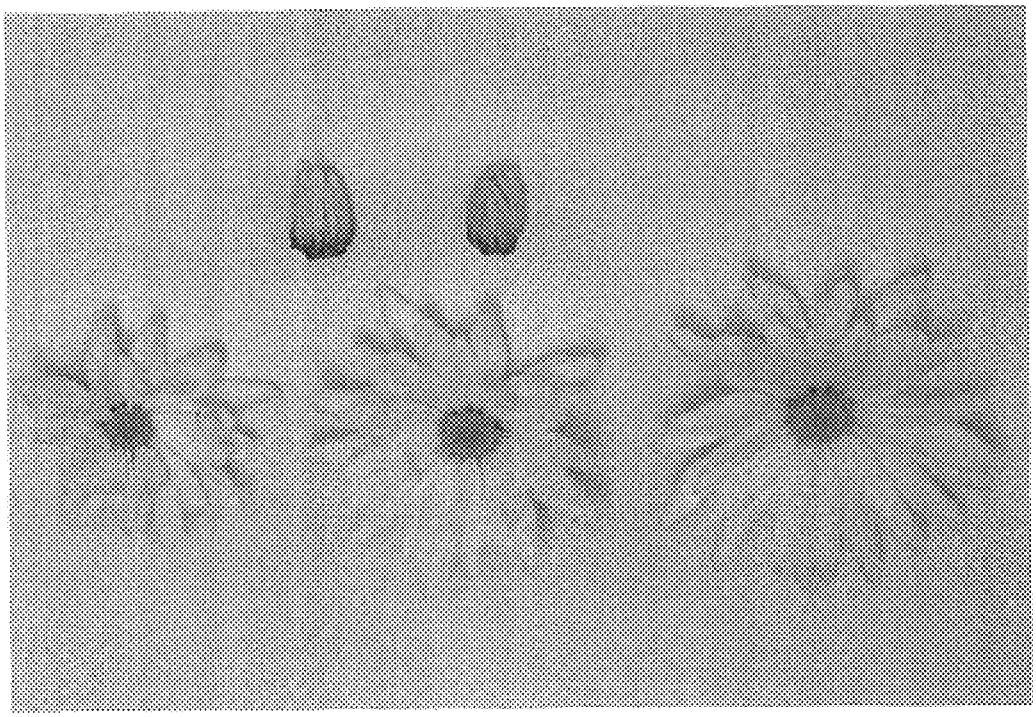
FIG. 2 shows the various stages of bloom of the new cultivar.
Figure 3:
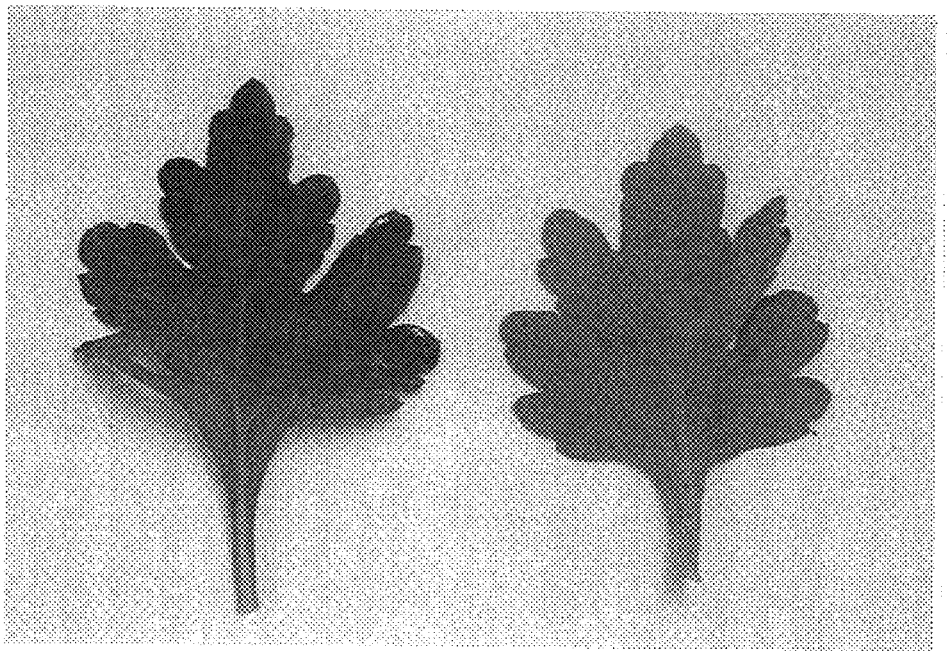
FIG. 3 shows the foliage of the new cultivar.

This new variety of chrysanthemum is of the botanical classification *Chrysanthemum morifolium*. The observations and measurements were gathered from plants grown in a greenhouse in Rijsenhout Holland in a photo-periodic controlled crop under conditions generally used in commercial practice. The greenhouse temperatures during this crop were at day-time between 18° C. and 25° C. and at night 20° C. The photo-periodic response time in this crop was 50 days after an average of eight long days. After this long day period to flowering growth retardants were applied 6 times in an average dose of 1.5 gram/liter water. The plants were observed (directly) during the flowering of this crop. No tests were done on disease or insect resistance or susceptibility. No tests were done on cold or drought tolerance. This new variety produces large sized blooms with huge yellow ray-florets and green disc-florets blooming on the plant for 5 weeks. This new variety of chrysanthemum has been found to retain its distinctive characteristics throughout successive propagations however the phenotype may vary significantly with variations in environment such as light intensity and temperature. To show the phenotype as described 'Powell' can be planted without assimilation lightning (high pressure sodium lamps) between week 50 and week 40 of the next year under greenhouse conditions in Holland. With assimilation lightning (minimum level 2500 lux) it can be planted year round under greenhouse conditions in Holland.

From the cultivars known to inventor the most similar existing cultivar in comparison to 'Powell' is 'Miramar' (U.S. Plant Pat. No. 7,469). When 'Miramar' and 'Powell' are being compared the following differences are noticed: The difference of 'Miramar' and 'Powell' are (1) flower color (2) flower shape and (3) Response time.

The following is a description of the plant and characteristics that distinguish 'Powell' as a new and distinct variety. The color designations are taken from the plant itself. Accordingly, any discrepancies between the color designations and the colors depicted in the photographs are due to photographic tolerances. The color chart used in this description is: The Royal Horticultural Society Colour Chart, edition 1995.

Botanical Description of Cultivar 'Powell'.

Bud:
*Size.*—Large;cross-section 1.4 cm, height 1.2 cm.
*Outside color.*—Yellow 13 B.
*Involucral bracts.*—2 rows, length 7 mm, width 3 mm.
*Involucral bracts among disc-florets.*—Not present.
*Involucral bracts color.*—Green 138 B.

Bloom:
*Type.*—Daisy.
*Height.*—Medium high.
*Size.*—Large.
*Fully expanded.*—8.0–8.5 cm.
*Number of blooms per branch.*—Approx. 3–4 blooms per branch.
*Performance on the plant.*—5 weeks.
*Seeds.*—Produced in large quantities, oval shaped, grey-brown 199A, 2 mm in length.
*Fragrance.*—Typical chrysanthemum.

Color:
*Center of the flower* (*disc-florets*).—Immature green 143 B. Mature yellow-green 151 A with a small dot of yellow-green 144 B.
*Color of upper surface of the ray-florets.*—Yellow 5 A.
*Color of the lower surface of the ray-florets.*—Yellow 6 C.
*Tonality from distance.*—A pot mum with huge yellow flowers and a green disc.
*Color of the surface of the ray-florets after aging of the plant.*—Yellow 5 B.

Ray florets:
*Texture.*—Upper and under side smooth.

Number:
*Cross-section.*—Convex.
*Longitudinal axis of majority.*—Reflexing and occasionally twisted.
*Length of corolla tube.*—Short.
*Ray-floret length.*—3.3–3.7 cm.
*Ray-floret width.*—1.3–1.5 cm.
*Ratio length/width.*—Low.
*Shape of tip.*—Pointed.

Disc florets:
*Disc diameter.*—1.0–1.2 cm.
*Distribution of disc florets.*—Numerous, clearly visible at all stages of flowering.
*Shape.*—Tubular.
*Color.*—Yellow-green 151 A.
*Receptacle shape.*—Conical raised.

Reproductive organs:
*Stamen* (*present in disc florets only*).—Very thin, 3 mm in length.
*Number of stamen.*—4.
*Stamen color.*—Green.
*Pollen.*—No pollen.
*Styles* (*present in both ray and disc florets*).—Thin.
*Style color.*—Yellow-green.
*Style length.*—4 mm.
*Stigmas.*—Yellow-green.
*Stigma width.*—1 mm.
*Ovaries.*—Enclosed in calyx.

Plant:
*Form.*—A pot mum meant for indoor use.
*Growth habit.*—Very spreading.
*Growth rate.*—Moderate.
*Height.*—26.0–28.0 cm.
*Width.*—28.0 cm.
*Stem color.*—Green 138 B.
*Stem strength.*—Very strong.
*Stem brittleness.*—Absent.
*Stem anthocyanin coloration.*—Absent.
*Length of lateral branch.*—From top to bottom 12.0–13.0 cm.
*Lateral branch color.*—Green 138 B.
*Lateral branch, attachment.*—Very strong.
*Branching* (*average number of lateral branches*).—Prolific with 6–7 breaks after pinching.
*Peduncle length.*—2.0–3.0 cm.
*Peduncle color.*—Green 138 B.
*Flowering response*(*photo-periodic controlled crop, not natural season*).—50 Days.

Foliage:
*Color mature.*—Upper side green 137 A. Under side green 138 A.
*Color immature.*—Upper side green 137 A. Under side green 138 A.
*Size.*—Large; length 10.5 cm, width 7.0 cm.
*Quantity* (*number per lateral branch*).—5–6.
*Shape.*—Oval and lobed.
*Texture upper side.*—Glabrous.
*Texture under side.*—Pubescent.
*Venation arrangement.*—Palmate.
*Shape of the margin.*—Lobed.
*Shape of base of sinus between lateral lobes.*—Acute.
*Margin of sinus between lateral lobes.*—Mostly diverging, sometimes converging.
*Shape of base.*—Acute sometimes truncate.
*Apex.*—Cuspidate.

Differences with the comparison varieties: When grown under the same conditions.

TABLE 1

| | 'Powell' | 'Miramar' |
|---|---|---|
| Flower color | Yellow 5A | Yellow 7A |
| Flower shape | Ray-florets reflexing and occasionally twisted | Straight |
| Response time | 50 days | 55 days |

I claim:

1. A new and distinct variety of chrysanthemum plant as described and illustrated.

* * * * *